(12) United States Patent
Kawai

(10) Patent No.: US 7,802,886 B2
(45) Date of Patent: Sep. 28, 2010

(54) OPHTHALMIC APPARATUS

(75) Inventor: Noriji Kawai, Gamagori (JP)

(73) Assignee: Nidek Co., Ltd., Gamagori-Shi (JP)

( * ) Notice: Subject to any disclaimer, the term of this patent is extended or adjusted under 35 U.S.C. 154(b) by 0 days.

(21) Appl. No.: 12/457,249

(22) Filed: Jun. 4, 2009

(65) Prior Publication Data
US 2009/0303439 A1    Dec. 10, 2009

(30) Foreign Application Priority Data
Jun. 5, 2008   (JP)   ............... 2008-147943

(51) Int. Cl.
*A61B 3/10*   (2006.01)
(52) U.S. Cl. .............. 351/211; 351/214; 351/221
(58) Field of Classification Search ............ 351/211, 351/214, 221, 212, 205, 246, 200
See application file for complete search history.

(56) References Cited

U.S. PATENT DOCUMENTS

| | | | | |
|---|---|---|---|---|
| 5,270,749 | A | * | 12/1993 | Okumura ............ 351/211 |
| 5,844,659 | A | * | 12/1998 | Isogai ............... 351/208 |
| 7,281,798 | B2 | | 10/2007 | Hanebuchi |
| 7,284,861 | B2 | | 10/2007 | Fujieda |
| 7,452,078 | B2 | | 11/2008 | Isogai |
| 2007/0008493 | A1 | | 1/2007 | Kratzer |

FOREIGN PATENT DOCUMENTS

| | | |
|---|---|---|
| JP | A-2003-164483 | 6/2003 |
| JP | A-2006-280613 | 10/2006 |
| JP | A-2007-089715 | 4/2007 |
| JP | A-2007-518500 | 7/2007 |

* cited by examiner

*Primary Examiner*—Hung X Dang
(74) *Attorney, Agent, or Firm*—Oliff & Berridge PLC

(57) ABSTRACT

An ophthalmic apparatus has an optical system for presenting a target to an examinee's eye through a lens, an optical system placed in an optical path of the target presenting optical system, for correcting a refractive error of the eye seeing the target, a switching unit arranged to switch an aperture size of a diaphragm, which is placed in a position substantially conjugate with a pupil with respect to the lens, between a first size corresponding to a pupil size of the eye in photopic vision and a second size larger than the pupil size in scotopic vision, an inputting unit arranged to generate a signal for switching the aperture size between the first and second sizes, and a control unit arranged to control driving of the switching unit based on the signal from the inputting unit to switch the aperture size between the first and second sizes.

9 Claims, 3 Drawing Sheets

OPHTHALMIC APPARATUS

BACKGROUND OF THE INVENTION

1. Field of the Invention

The present invention relates to an ophthalmic apparatus such as an eye refractive power measurement apparatus which measures eye refractive power of an examinee's eye.

2. Description of Related Art

Conventionally, in order to obtain an estimate of a corrective diopter when prescribing a corrective such as spectacles, there is used an eye refractive power measurement apparatus which projects light of a measurement target onto a fundus of an examinee's eye, detects the light reflected from the fundus by a photodetector, and measures eye refractive power of the eye based on a result of the detection (see Japanese Patent Application Unexamined Publication No. 2007-89715 (corresponding to U.S. Pat. No. 7,452,078)). In addition, there is known an eye refractive power measurement apparatus in which a target presenting optical system includes an optical system for correcting a spherical refractive error and an astigmatic refractive error of an examinee's eye (see Japanese Patent Application Unexamined Publication No. 2006-280613 (corresponding to U.S. Pat. No. 7,281,798)).

Visual acuity of an eye can vary depending on an ambient brightness. This is because a pupil size of the eye varies depending on the ambient brightness, so that its optical aperture effect varies a depth of field, or that aspherical properties of a cornea and a crystalline lens cause different influences of aberrations. At dusk or night (scotopic vision), the pupil size is increased, and accordingly visual acuity varies, so that enough visual acuity cannot be obtained by using a corrective such as spectacles which has been prescribed in consideration of a daytime brightness (photopic vision).

In order to check a difference between visual acuity in the scotopic vision and visual acuity in the photopic vision, a visual acuity test is performed while actually changing the ambient brightness by using a target presenting apparatus separate from the eye refractive power measurement apparatus. However, it is necessary to wait for adaptation of the pupil size to the ambient brightness, and therefore, the test takes a long time and an immediate comparison of visibilities in the scotopic vision and in the photopic vision cannot be performed. In addition, when the ambient brightness is changed from the scotopic vision to the photopic vision, the examinee perceives glare.

SUMMARY OF THE INVENTION

An object of the invention is to overcome the problems described above and to provide an ophthalmic apparatus which allows for easy checking of a difference between visibilities in scotopic vision and in photopic vision and allows an examinee to recognize the necessity to change a corrective diopter in the scotopic vision with respect to a corrective diopter in the photopic vision.

To achieve the objects and in accordance with the purpose of the present invention, an ophthalmic apparatus has a target presenting optical system for presenting a target to an examinee's eye through a lens, a correction optical system placed in an optical path of the target presenting optical system, for correcting a refractive error of the eye seeing the target, a diaphragm switching unit arranged to switch an aperture size of a diaphragm, which is placed in a position substantially conjugate with a pupil of the eye with respect to the lens, between a first size corresponding to a pupil size of the eye in photopic vision and a second size larger than the pupil size of the eye in scotopic vision, a switching signal inputting unit arranged to generate a switching signal for switching the aperture size of the diaphragm between the first size and the second size, and a diaphragm control unit arranged to control driving of the diaphragm switching unit based on the switching signal from the switching signal inputting unit to switch the aperture size of the diaphragm between the first size and the second size.

Yet, in another aspect of the present invention, an ophthalmic apparatus further has an eye refractive power measurement unit which comprises an eye refractive power measurement optical system for projecting light of a measurement target onto a fundus of an examinee's eye and photo-receiving the light reflected from the fundus by a photodetector, and is arranged to obtain eye refractive power of the eye based on output from the photodetector, a target presenting optical system for presenting a target to the eye through a lens, a correction optical system placed in an optical path of the target presenting optical system, for correcting a refractive error of the eye seeing the target, a diaphragm switching unit arranged to switch an aperture size of a diaphragm, which is placed in a position substantially conjugate with a pupil of the eye with respect to the lens, between a first size corresponding to a pupil size of the eye in photopic vision and a second size larger than the pupil size of the eye in scotopic vision, a switching signal inputting unit arranged to generate a switching signal for switching the aperture size of the diaphragm between the first size and the second size, a mode setting unit arranged to input a setting signal for establishing a checking mode for checking visibilities in the scotopic vision and the photopic vision after measuring the eye refractive power, a correction optical system control unit arranged to control driving of the correction optical system based on the eye refractive power obtained by the eye refractive power measurement unit when the checking mode is established, and a diaphragm control unit arranged to control driving of the diaphragm switching unit based on the switching signal from the switching signal inputting unit to switch the aperture size of the diaphragm between the first size and the second size when the checking mode is established.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
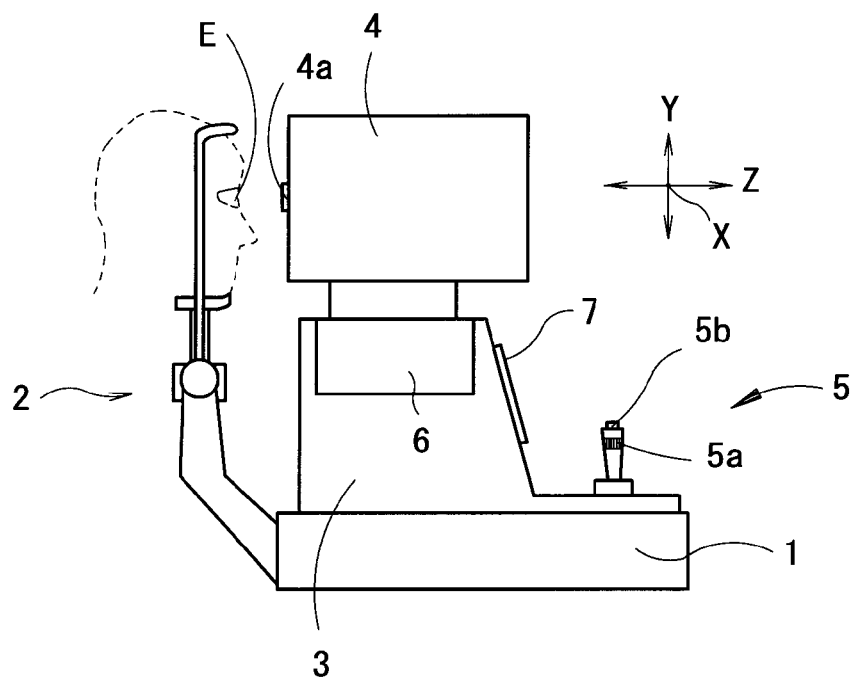
FIG. 1 is a schematic external view of an eye refractive power measurement apparatus.

A detailed description of one preferred embodiment of an ophthalmic apparatus embodied by the present invention is provided below with reference to the accompanying drawings. FIG. 1 is a schematic external view of an eye refractive power measurement apparatus. The apparatus includes a base 1, a face supporting unit 2 attached to the base 1, a mobile base 3 movable on the base 1, and a measurement unit 4 movable on the mobile base 3 and housing an optical system to be described later. The measurement unit 4 is moved in a right/left direction (an X direction), an up/down direction (a Y direction), and a back/forth direction (a Z direction) with respect to an examinee's eye E by an XYZ driving unit 6 provided to the mobile base 3. The mobile base 3 is moved in the X and Z directions on the base 1 by operation of a joystick 5. The measurement unit 4 is moved in the Y direction by means of the XYZ driving unit 6 through rotating operation of a rotation knob 5a by an examiner. A measurement starting switch 5b is provided at the tip of the joystick 5. A display monitor 7 is provided to the mobile base 3.

Figure 2:
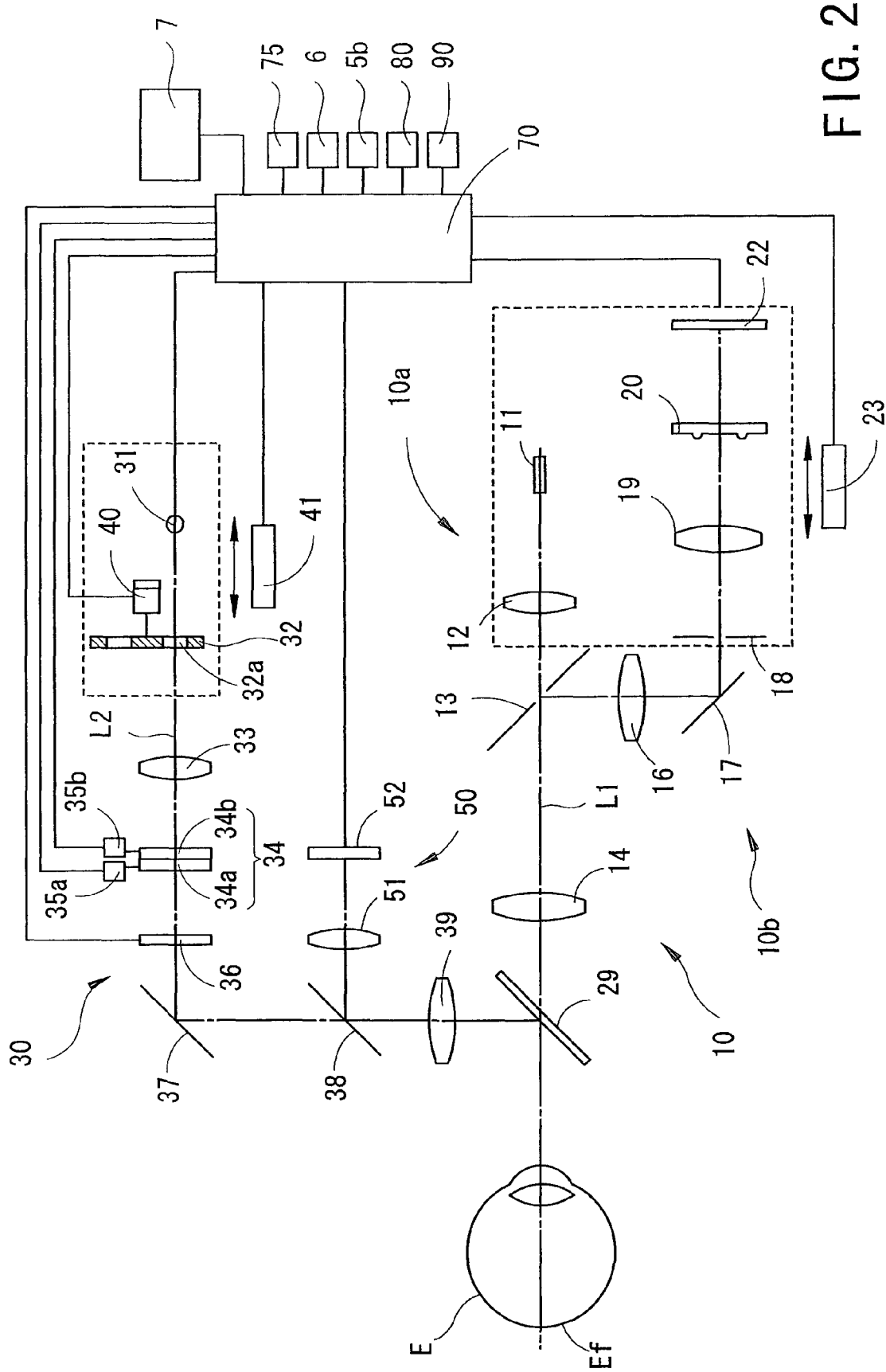
FIG. 2 is a schematic view showing an optical system and a control system of the eye refractive power measurement apparatus.

FIG. 2 is a schematic view showing an optical system and a control system of the apparatus. A measurement optical system 10 includes a projection optical system 10a for projecting light of a measurement target in a spot shape onto a fundus Ef through a central pupillary portion of the eye E, and a photo-receiving optical system 10b for making the light which is reflected from the fundus Ef and passes through a peripheral pupillary portion into a ring shape and picking up a ring-shaped fundus reflection image by a two-dimensional image-pickup element.

The projection optical system 10a includes a measurement light source 11, a relay lens 12, a hole mirror 13, and a measurement objective lens 14, which are disposed on an optical axis L1 of the measurement optical system 10. The light source 11 has an optically conjugate relation with the fundus Ef of the eye E with emmetropia. An opening of the hole mirror 13 has an optically conjugate relation with a pupil of the eye E.

The photo-receiving optical system 10b shares the objective lens 14 and the hole mirror 13 with the projection optical system 10a, and includes a relay lens 16 and a total reflection mirror 17 which are disposed on the optical axis L1 in a reflecting direction of the hole mirror 13, and a photo-receiving diaphragm 18, a collimator lens 19, a ring lens 20, and a two-dimensional image-pickup element 22 which are disposed on the optical axis L1 in a reflecting direction of the total reflection mirror 17. The photo-receiving diaphragm 18 and the image-pickup element 22 have an optically conjugate relation with the fundus Ef. The ring lens 20 includes a lens portion where a cylindrical lens in a ring shape is formed on one side of a transparent plate, and light shielding portions which are provided to other portion than the ring-shaped lens, and has an optically conjugate relation with the pupil. Output from the image-pickup element 22 is inputted to a control unit 70. The light source 11 and the relay lens 12 of the projection optical system 10a, and the collimator lens 19, the ring lens 20, and the image-pickup element 22 of the photo-receiving optical system 10b are integrally moved in the optical axis L1 direction by a moving mechanism 23. The measurement optical system 10 is not limited to the above-described one, and known ones may be used.

A dichroic mirror 29 is disposed between the objective lens 14 and the eye E. The dichroic mirror 29 guides light of a target from a target presenting optical system 30 to the eye E and guides the light reflected from an anterior segment of the eye E to an observation optical system 50. The dichroic mirror 29 has a property of transmitting light having a wavelength equivalent to a wavelength of the measurement light of the measurement optical system 10.

The observation optical system 50 includes an image-pickup lens 51 and a two-dimensional image-pickup element 52 which are disposed on an optical axis in a reflecting direction of a half mirror 38. Output from the image-pickup element 52 is inputted to the control unit 70. Thus, an image of the anterior segment is picked up by the image-pickup element 52 and is displayed on the monitor 7.

The target presenting optical system 30 shares an objective lens 39 with the observation optical system 50, and includes a light source 31 such as an LED, a target plate 32, a relay lens 33, a variable aperture diaphragm 36, and a total reflection mirror 37 which are disposed on an optical axis L2 which is made coaxial with the optical axis L1 by the dichroic mirror 29. The target presenting optical system 30 also acts as an eye refractive power correction optical system for correcting eye refractive power of the eye E, and an astigmatism correction optical system 34 is disposed between the diaphragm 36 and the relay lens 33.

The target plate 32 has a concentric arrangement of a fixation target for fogging the eye E in objective measurement and a plurality of targets 32a including visual acuity test optotypes used in subjective measurement. The visual acuity test optotypes of respective visual acuity values (0.1, 0.3 . . . 1.5) are available. The target plate 32 is rotated by a motor 40 to change the target 32a to be placed on the optical axis L2 of the target presenting optical system 30. Light of the target 32a illuminated by the light source 31 passes through the relay lens 33 through the dichroic mirror 29 to be headed to the eye E.

The light source 31 and the target plate 32 (the target 32a) are integrally moved in the optical axis L2 direction by a driving mechanism 41 comprised of a motor and a sliding mechanism. In the objective measurement, the movement of the light source 31 and the target 32a fogs the eye E. In the subjective measurement, a presenting position (a presenting distance) of the target 32a with respect to the eye E is optically changed, so that sphere power of the eye E is corrected. In other words, the movement of the objective lens 39, the relay lens 33, the light source 31, and the target 32a defines a sphere power correction optical system.

The astigmatism correction optical system 34 includes two positive cylindrical lenses 34a and 34b whose focal lengths are equal. The cylindrical lenses 34a and 34b are independently rotated about the optical axis L2 by driving of rotating mechanisms 35a and 35b, respectively. For a correction optical system in the subjective measurement, the astigmatism correction optical system 34 is preferably provided. However, in a simplified configuration for comparing visibilities in photopic vision and in scotopic vision to be described later, using only the sphere power correction optical system is sufficient. In the case of using the sphere power correction optical system, spherical equivalent power which is obtained by adding a half of an astigmatic refractive error to a spherical refractive error is used for correction. In addition, the correction optical system may be configured by inserting and removing a correction lens in an optical path of the target presenting optical system 30. The sphere power correction optical system may be configured by adding a relay lens movable in the optical axis L2 direction to the target presenting optical system 30.

Figure 3:
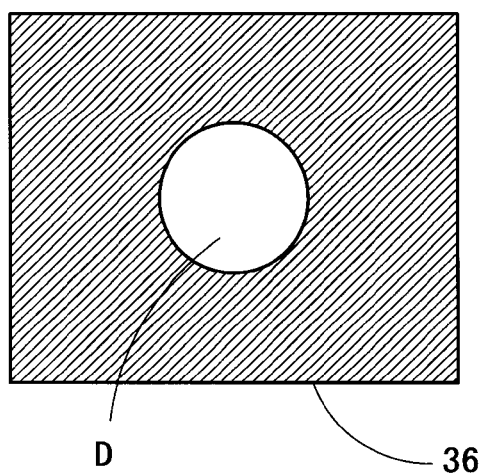
FIG. 3 shows an example of a variable aperture diaphragm.

The diaphragm 36 is placed in a position substantially conjugate with the pupil with reference to the objective lens 39. For the diaphragm 36, a liquid crystal display is used herein. Display on the liquid crystal display is controlled by the control unit 70, and a size of a circular light transmitting region D (an aperture size) having the optical axis L2 at the center is variable (see FIG. 3). An outer region of the light transmitting region D defines a light shielding region. The size of the light transmitting region D (the aperture size) is switchable between a size D1 corresponding to the pupil size of the eye E in the photopic vision (e.g. 3 mm in diameter) and a size D2 larger than the pupil size of the eye E in the scotopic vision (e.g. 10 mm in diameter). The sizes D1 and D2 define sizes on the pupil, and an actual aperture size of the diaphragm 36 is determined by magnification of the target presenting optical system 30 using the objective lens 39 and the other constituent elements. The diaphragm 36 is not limited to the liquid crystal display and may be defined by two diaphragms having aperture sizes corresponding to the sizes D1 and D2, respectively, which are selectively placed on the optical path. The diaphragm 36 maybe defined by a diaphragm whose aperture size is continuously variable. The switching of the aperture size of the diaphragm 36 to the size D2 includes insertion and removal of the diaphragm 36 having the aperture size corresponding to the size D1 into and from the optical path.

Figure 4:
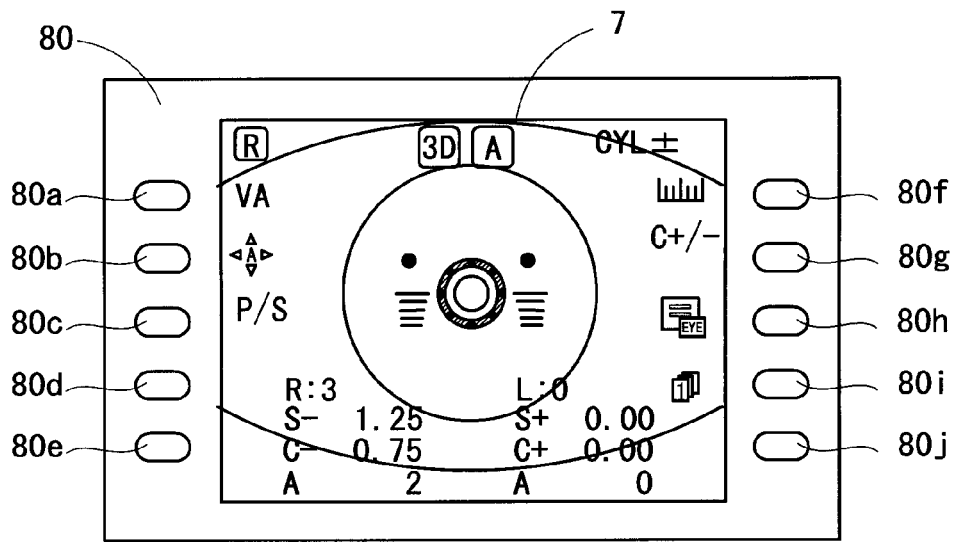
FIG. 4 is a view for illustrating a display on a monitor in an objective measurement mode and a layout of a switch unit.

The control unit 70 is connected with the image-pickup element 22 and performs arithmetic processing of the eye refractive power based on the output from the image-pickup element 22. The control unit 70 is also connected with the image-pickup element 52, the moving mechanism 23, the driving mechanism 41, the motor 40, the light source 31, the rotation mechanisms 35a and 35b, the monitor 7, a switch unit 80 having a plurality of switches and used for performing various settings for measurement, the measurement starting switch 5b, a memory 75, the XYZ driving unit 6, a printer 90, and other constituent elements. FIG. 4 is a view for illustrating a display on the monitor 7 in an objective measurement mode and a layout of the switch unit 80. The switch unit 80 has switches 80a, 80b, 80c, 80d, and 80e which are disposed on the left side of the screen of the monitor 7, and switches 80f, 80g, 80h, 80i, and 80j which are disposed on the right side of the screen of the monitor 7. The capabilities of signals from the switches 80a to 80j are changed corresponding to icons which are displayed lateral to the switches in each measurement mode.

Next, a description of a measurement operation of the apparatus having the configuration described above will be provided. The apparatus is placed in the objective measurement mode at the time of start-up. The aperture size of the diaphragm 36 in the objective measurement mode is the size D2 for the scotopic vision (10 mm) or maximum. As the target 32a of the target presenting optical system 30, the fixation target for the objective measurement for fogging the eye E is placed on the optical path. The examiner fixes the face of the examinee by the face supporting unit 2 and makes the examinee fixate the fixation target in the measurement unit 4 through a measurement window 4a of the measurement unit 4 (see FIG. 1). The cabinet of the measurement unit 4 is positioned in front of the examinee's eyes (the examinee's side of the cabinet of the measurement unit 4 is large enough to shield the examinee's eyes), and the fixation target for the objective measurement is presented at a luminance of about 25 cd/m$^2$, so that a naturally dilated state in which the pupil naturally dilates (corresponding to the scotopic vision) is achieved during the objective measurement.

At the time of the objective measurement, the anterior-segment image picked up by the image-pickup element 52 of the observation optical system 50 is displayed on the monitor 7. The examiner observes the anterior-segment image, an alignment target image (not shown), and a reticle mark (not shown) on the monitor 7 and moves the measurement unit 4 and the mobile base 3 by operation of the joystick 5 and the other constituent elements in order to perform alignment of the eye E with the optical system of the apparatus to bring them into a given positional relation. Upon completion of the alignment, a measurement starting signal is inputted from the measurement starting switch 5b in order to perform the objective measurement.

The measurement light emitted from the light source 11 passes through the relay lens 12 through the dichroic mirror 29 to be projected onto the fundus Ef and form a point light source image in a spot shape on the fundus Ef. The light forming the point light source image on the fundus Ef is reflected and scattered from the fundus Ef to exit the eye E, is collected by the objective lens 14, passes through the hole mirror 13 through the total reflection mirror 17, is collected again by an aperture of the photo-receiving diaphragm 18, is made into substantially parallel light by the collimator lens 19 (in the case of emmetropia), is received by the ring lens 20 to be made into ring-shaped light, and is photo-received as a ring image on the image-pickup element 22.

First, preliminary measurement of eye refractive power is performed. The light source 31 and the target plate 32 are moved in the optical axis L2 direction based on a result of the preliminary measurement in order to place the fixation target in a position substantially conjugate with the fundus Ef. Then, the light source 31 and the target plate 32 are moved further in the optical axis L2 direction in order to fog the eye E by an adequate diopter. With the eye E being fogged, the ring image photo-received on the image-pickup element 22 is detected and processed, and the control unit 70 calculates the eye refractive power (sphere power S, astigmatic power C, and an astigmatic axial angle A).

Figure 5:
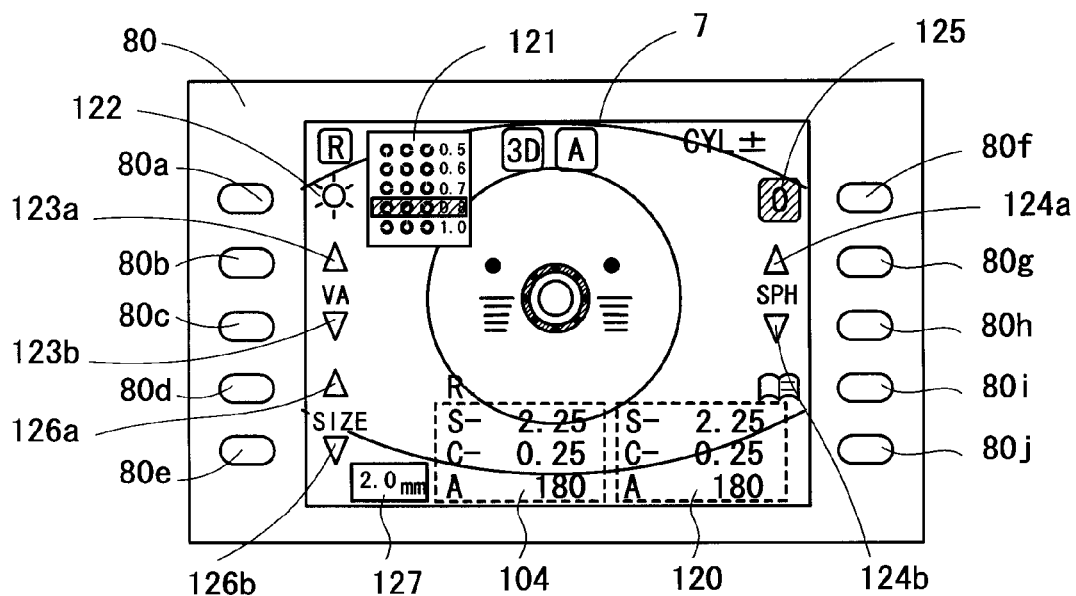
FIG. 5 is a view for illustrating a photopic/scotopic vision checking mode.

A photopic/scotopic vision checking mode becomes selectable after the objective measurement. In the screen for the objective measurement mode in FIG. 4, when the switch 80c corresponding to an icon "P/S" is pressed, the screen of the monitor 7 enters the photopic/scotopic vision checking mode as shown in FIG. 5. In the photopic/scotopic vision checking mode in FIG. 5, the switch 80a corresponding to an icon 122 allows for input of selection signals of a photopic vision mode and a scotopic vision mode. When the screen of the monitor 7 enters the photopic/scotopic vision checking mode, the correction optical system is driven based on a result of the objective measurement so as to correct a refractive error of the eye E. In other words, the light source 31 and the target plate 32 are moved in the optical axis L2 direction based on the sphere power S obtained by the objective measurement so as to bring about a state in which a spherical refractive error is corrected, and the astigmatism correction optical system 34 is driven based on the astigmatic power C and the astigmatic axial angle A obtained by the objective measurement so as to bring about a completely corrected state in which an astigmatic refractive error is corrected. In comparing the visibilities in the photopic vision and in the scotopic vision, the correction of the astigmatic refractive error is not necessarily performed, and it is essential only that at least the spherical refractive error is corrected.

For the target 32a of the target presenting optical system, not only the fixation target used in the objective measurement but also the visual acuity test optotypes used in the subjective measurement are selectable by the switches 80b and 80c corresponding to icons 123a and 123b. In the same manner as the objective measurement, the luminance of the target 32a in the photopic/scotopic vision checking mode is set such that the pupil is not contracted. To be specific, the luminance of the target 32a is set to be about 25 cd/m$^2$ equivalent to dusk brightness.

When the screen of the monitor 7 enters the photopic/scotopic vision checking mode, the photopic vision mode is established first. Once the photopic vision mode is established, the aperture size of the diaphragm 36 placed in the optical path of the target presenting optical system 30 is switched to the size D1 corresponding to the pupil size of the eye E in the photopic vision (3 mm in diameter) The switching of the aperture size of the diaphragm 36, which is placed in the position substantially conjugate with the eye E, to the size D1 allows the examinee to experience the visibility of the target 32a while having the pupil size of the eye E in the photopic vision (the pupil in a contracted condition) without actually contracting the pupil.

Next, the switch 80a is pressed on the screen of the monitor 7 shown in FIG. 5 to establish the scotopic vision mode, and the aperture size of the diaphragm 36 is switched to the size D2 larger than the pupil size of the eye E in the scotopic vision (10 mm in diameter). The pupil of the eye E is in the naturally dilated state during the subjective measurement, and therefore, the switching of the aperture size of the diaphragm 36 to the size larger than the pupil size of the eye E whose pupil is in the naturally dilated state makes the examinee see the target 32a in the scotopic vision. Each time the switch 80a is pressed, the aperture size of the diaphragm 36 is switched to immediately switch between the photopic vision and the scotopic vision, so that the examinee is allowed to experience the difference between the visibilities in the photopic vision and the scotopic vision.

In a simplified configuration for comparing the visibilities in the photopic vision and in the scotopic vision, the fixation target may be used as the target 32a of the target presenting optical system 30 in the same manner as the objective measurement. However, the use of the subjective measurement target as the target 32a allows the examinee to experience more accurately the difference between the visibilities in the photopic vision and in the scotopic vision.

Figure 6:
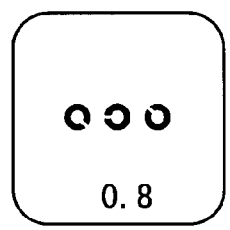
FIG. 6 shows an example of a target to be presented to an examinee's eye.

A description of the subjective measurement using the subjective measurement target will be provided. A description of the subjective measurement in the photopic vision mode is firstly provided. First, optotypes of a visual acuity value of 0.8, for example, are presented by using the switches 80b and 80c (see FIG. 6). The examiner checks if the examinee can read the optotypes, and varies the visual acuity value by pressing the switches 80b and 80c based on a response from the examinee. When the switch 80b is pressed, the control unit 70 controls the motor 40 to rotate the target plate 32 and place on the optical axis L2 optotypes of a visual acuity value which is one step lower than the previous value. When the switch 80c is pressed, the control unit 70 controls the motor 40 to rotate the target plate 32 and place on the optical axis L2 optotypes of a visual acuity value which is one step higher than the previous value. The examiner repeats this subjective measurement and obtains the highest one of the visual acuity values at which the examinee can read the optotypes. In a visual acuity target display section 121, the visual acuity test optotypes currently presented and their visual acuity value are displayed.

Then, the examiner adjusts the sphere power of the correction optical system in order that the sphere power S to be applied to the eye E in the state where the highest visual acuity value is obtained may become weakest (closer to the positive side). The sphere power is adjusted by moving the light source 31 and the target plate 32 in the optical axis L2 direction based on signals from the switches 80g and 80h corresponding to icons 124a and 124b for adjusting the sphere power of the correction optical system. Corrective diopters obtained by the subjective measurement are displayed in a display field 120 located at the lower right of the screen, and corrective diopters obtained by the objective measurement are displayed in a display field 104 on the left side of the display field 120 at the lower portion of the screen.

In the subjective measurement, a result of the subjective measurement in the photopic vision mode (the visual acuity value of the target 32a finally presented and the corrective diopters displayed in the display field 120) are stored in the memory 75 based on a signal for exiting the photopic vision mode, for example, when the measurement mode is switched by the switch 80a, and when the switch 80f corresponding to an icon 125 for establishing the objective measurement mode is pressed.

Then, the examiner establishes the scotopic vision mode by pressing the switch 80a. When the scotopic vision mode is established, the target 32a of the target presenting optical system 30 and the corrective diopters of the correction optical system remain unchanged from those at the time of the subjective measurement in the photopic vision mode, while the aperture size of the diaphragm 36 placed in the optical path of the target presenting optical system 30 is switched. The aperture size of the diaphragm 36 in the scotopic vision mode is switched to the size D2 larger than the pupil size of the eye E in the scotopic vision (10 mm in diameter). The switching of the aperture size of the diaphragm 36 to the size larger than the pupil size of the eye E whose pupil is in the naturally dilated state allows the examinee to see the target 32a in the scotopic vision.

As described above, the examiner changes the photopic vision mode to the scotopic vision mode in order to check if the examinee finds a difference between the visibilities in the photopic vision and in the scotopic vision. In a conventional manner of changing an ambient brightness so that the pupil size of the eye E is actually varied between the scotopic vision and the photopic vision, it is necessary to wait for adaptation of the pupil size of the eye E to the ambient brightness. Thus, an immediate comparison is difficult. In addition, the examinee has difficulty in finding the difference. In contrast, the switching of the aperture size of the diaphragm 36 from the size D1 to the size D2 immediately changes the display of the target 32a in the photopic vision to the display of the target 32a in the scotopic vision, so that the examinee is allowed to compare and check the difference between the visibilities in the scotopic vision and in the photopic vision. Each time the switch 80a is pressed, the aperture size of the diaphragm 36 is alternately switched between the size D1 and the size D2, which allows the examinee to easily check the difference between the visibilities in the scotopic vision and in the photopic vision.

When the visibility in the scotopic vision is inferior to the visibility in the photopic vision, the examiner performs the visual acuity measurement in the scotopic vision in a similar manner to the above-described measurement. The target 32a to be placed on the optical path of the target presenting optical system 30 is changed by pressing the switches 80b and 80c. While receiving a response from the examinee, the examiner obtains the highest one of the visual acuity values at which the examinee can read the target 32a. The sphere power of the correction optical system is varied based on switch signals from the switches 80*g* and 80*h*. The examiner adjusts the sphere power of the correction optical system in order that the sphere power S to be applied to the eye E may become weakest while the highest visual acuity value is kept unchanged. Accordingly, the sphere power S is measured and a result of the measurement is displayed in the display field 120. If the corrective diopter in the scotopic vision is different from the corrective diopter in the photopic vision, the examinee recognizes the necessity to change the corrective diopter in the scotopic vision in a corrective which has been prescribed for the photopic vision.

When the difference between the corrective diopter in the photopic vision and the corrective diopter in the scotopic vision which is calculated by the control unit 70 is more than a given diopter (e.g. 0.5 D), an indication informing as such is displayed on the screen of the monitor 7. Thus, the examiner is allowed to recognize the necessity of a corrective for the scotopic vision in addition to the corrective for the photopic vision. When the switch 80*f* for exiting the subjective measurement in FIG. 5 is pressed, data of the visual acuity values and the corrective diopters in the photopic vision and in the scotopic vision is stored in the memory 75, and the data is outputted from the printer 90 by pressing a printout switch not shown.

At the time of switching the aperture size of the diaphragm 36 in the configuration described above, the intensity of the target light is preferably adjusted in accordance with the aperture size D in order that the intensity of the target light entering the eye E through the pupil may be maintained substantially constant. The intensity of the target light is adjusted by changing the luminance of the light emitted from the light source 31 illuminating the target 32*a*. When the luminance of the light emitted from the light source 31 is maintained constant, the switching of the aperture size of the diaphragm 36 from the size D1 for the photopic vision to the size D2 for the scotopic vision larger than the size D1 increases the intensity of the target light passing through the aperture of the diaphragm 36, so that the examinee perceives the target 32*a* as bright in such a state that the luminance of the target 32*a* is increased. In such a case, presenting conditions of the target 32*a* in the scotopic vision and in the photopic vision are different, and accordingly, accuracy of the measurement is somewhat decreased. In addition, enlarging the aperture size of the diaphragm 36 could make the examinee perceive glare. In order to prevent such problems, at the time of switching the aperture size of the diaphragm 36 from the size D1 to the size D2, the control unit 70 changes the intensity of the light emitted from the light source 31 in accordance with the change ratio between aperture areas. To be specific, when the size D1 is 3 mm and the size D2 is 10 mm, the change ratio of the aperture area of the size D1 for the photopic vision to the aperture area of the size D2 for the scotopic vision is 0.09. Therefore, at the time of switching the aperture size of the diaphragm 36, the control unit 70 adjusts the intensity of the light emitted from the light source 31 to 0.09. In this way, the intensity of the target light passing through the diaphragm 36 is maintained substantially constant.

Actual pupil sizes of eyes in the scotopic vision differ among examinees. Therefore, the above-described adjustment of the intensity of the target light in the scotopic vision is preferably performed while obtaining an actual pupil size of the eye E. A description thereof will be provided as an example. The image of the anterior segment including the pupil is picked by the image-pickup element 52 of the observation optical system 50 at the time of the refractive power measurement, and data of the anterior-segment image is stored in the memory 75 of the control unit 70. The control unit 70 performs image processing on the anterior-segment image and extracts a pupil area in order to obtain the pupil size. When the aperture size of the diaphragm 36 is switched to the size D2 for the scotopic vision, the ratio between the aperture area of the diaphragm 36 in the photopic vision and the pupil area obtained from the anterior-segment image is calculated, and the intensity of the target light (the luminance of the light source 31) is adjusted in accordance with the calculated ratio.

In the description provided above, the size D1 for the photopic vision of the diaphragm 36 is a pupil size of a normal human eye (3 mm). However, if the actual pupil size of the eye E in the photopic vision is previously known, the aperture size of the diaphragm 36 may be adjusted in accordance with the actual pupil size. In the screen for the photopic vision mode in FIG. 5, icons 126*a* and 126*b* for inputting the pupil size are provided. A display field 127 in which the pupil size inputted by using the switches 80*d* and 80*e* is displayed is provided in the vicinity of the icons 126*a* and 126*b*. When the switch 80*d* is pressed, the pupil size is increased in given steps, and when the switch 80*e* is pressed, the pupil size is decreased in given steps. The inputted pupil size is checked by referring to the display field 127. When the photopic vision mode is selected by using the switch 80*a*, the control unit 70 adjusts the aperture size of the diaphragm 36 based on the pupil size inputted by using the switches 80*d* and 80*e*.

The adjustment of the aperture size of the diaphragm 36 in the photopic vision mode may be performed also in such a manner that the eye E is previously actually brought into the photopic vision, and the control unit 70 extracts the pupil area from the anterior-segment image picked up by the image-pickup element 52 of the observation optical system 50 as described above and automatically adjusts the aperture size of the diaphragm 36 based on the pupil size.

After checking the visibilities in the photopic vision and in the scotopic vision, the apparatus may perform normal subjective refractive power measurement with the luminance of the target 32*a* in a bright state. The normal subjective refractive power measurement is enabled by pressing the switch 80*a* corresponding to an icon "VA" on the screen of the monitor 7 shown in FIG. 4. The operation of the subjective refractive power measurement is well known, and a description thereof is omitted.

The eye refractive power measurement apparatus having the functions described above allows for pseudo switching between the photopic vision and the scotopic vision without actually contracting or dilating the pupil, and facilitates checking the difference between the visibilities in the photopic vision and in the scotopic vision within a short period of time. In addition, the eye refractive power measurement apparatus having the functions described above allows the examinee to recognize the necessity to change the corrective diopters in the scotopic vision with respect to the corrective diopters in the photopic vision.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
a target presenting optical system for presenting a target to an examinee's eye through a lens;
a correction optical system placed in an optical path of the target presenting optical system, for correcting a refractive error of the eye seeing the target;
a diaphragm switching unit arranged to switch an aperture size of a diaphragm, which is placed in a position substantially conjugate with a pupil of the eye with respect to the lens, between a first size corresponding to a pupil size of the eye in photopic vision and a second size larger than the pupil size of the eye in scotopic vision;
a switching signal inputting unit arranged to generate a switching signal for switching the aperture size of the diaphragm between the first size and the second size; and
a diaphragm control unit arranged to control driving of the diaphragm switching unit based on the switching signal from the switching signal inputting unit to switch the aperture size of the diaphragm between the first size and the second size.

2. The ophthalmic apparatus according to claim 1, wherein the diaphragm switching unit comprises any one of:
(a) the diaphragm having a variable aperture size, wherein the diaphragm switching unit is arranged to selectively vary the aperture size of the diaphragm between the first size and the second size;
(b) the diaphragm defined by a first diaphragm having an aperture size corresponding to the first size and a second diaphragm having an aperture size corresponding to the second size, wherein the diaphragm switching unit is arranged to selectively place the first diaphragm and the second diaphragm in the optical path; and
(c) the diaphragm having an aperture size corresponding to the first size, wherein the diaphragm switching unit is arranged to insert and remove the diaphragm into and from the optical path, and an aperture size on the optical path when the diaphragm is removed from the optical path defines the second size.

3. The ophthalmic apparatus according to claim 1, wherein the diaphragm switching unit comprises:
the diaphragm defined by a variable aperture diaphragm comprised of a display arranged to form a transmitting region and a shielding region for light of the target, wherein the diaphragm switching unit is arranged to selectively vary a size of the transmitting region between the first size and the second size.

4. The ophthalmic apparatus according to claim 1, wherein the target presenting optical system comprises:
a light source which illuminates the target, wherein a luminance of the target illuminated by the light source is equivalent to a dusk brightness.

5. The ophthalmic apparatus according to claim 1, wherein the target presenting optical system comprises:
a light source which illuminates the target, and the apparatus further comprises:
an intensity adjusting unit arranged to adjust intensity of light from the light source based on the aperture size of the diaphragm switched by the diaphragm switching unit so as to maintain intensity of light of the target passing through an aperture of the diaphragm having each of the first size and the second size constant.

6. The ophthalmic apparatus according to claim 1, wherein the target presenting optical system comprises:
a light source which illuminates the target, and the apparatus further comprises:
an image-pickup optical system comprising an image-pickup element which picks up an image of an anterior segment of the eye including the pupil in a state that a luminance of the target illuminated by the light source is equivalent to a dusk brightness;
a pupil size obtaining unit arranged to obtain a size of the pupil by processing the anterior-segment image picked up by the image-pickup element; and
an intensity adjusting unit arranged to adjust intensity of light from the light source based on the first size and the pupil size obtained by the pupil size obtaining unit so as to maintain intensity of light of the target passing through an aperture of the diaphragm having each of the first size and the pupil size constant.

7. The ophthalmic apparatus according to claim 1, further comprising:
an eye refractive power measurement unit which comprises an eye refractive power measurement optical system for projecting light of a measurement target onto a fundus of the eye and photo-receiving the light reflected from the fundus by a photodetector, and is arranged to obtain eye refractive power of the eye based on output from the photodetector; and
a correction optical system control unit arranged to control driving of the correction optical system based on the eye refractive power obtained by the eye refractive power measurement unit.

8. An ophthalmic apparatus comprising:
an eye refractive power measurement unit which comprises an eye refractive power measurement optical system for projecting light of a measurement target onto a fundus of an examinee's eye and photo-receiving the light reflected from the fundus by a photodetector, and is arranged to obtain eye refractive power of the eye based on output from the photodetector;
a target presenting optical system for presenting a target to the eye through a lens;
a correction optical system placed in an optical path of the target presenting optical system, for correcting a refractive error of the eye seeing the target;
a diaphragm switching unit arranged to switch an aperture size of a diaphragm, which is placed in a position substantially conjugate with a pupil of the eye with respect to the lens, between a first size corresponding to a pupil size of the eye in photopic vision and a second size larger than the pupil size of the eye in scotopic vision;
a switching signal inputting unit arranged to generate a switching signal for switching the aperture size of the diaphragm between the first size and the second size;
a mode setting unit arranged to input a setting signal for establishing a checking mode for checking visibilities in the scotopic vision and the photopic vision after measuring the eye refractive power;
a correction optical system control unit arranged to control driving of the correction optical system based on the eye refractive power obtained by the eye refractive power measurement unit when the checking mode is established; and
a diaphragm control unit arranged to control driving of the diaphragm switching unit based on the switching signal from the switching signal inputting unit to switch the aperture size of the diaphragm between the first size and the second size when the checking mode is established.

9. The ophthalmic apparatus according to claim 8, wherein the diaphragm switching unit comprises any one of:

(a) the diaphragm having a variable aperture size, wherein the diaphragm switching unit is arranged to selectively vary the aperture size of the diaphragm between the first size and the second size;
(b) the diaphragm defined by a first diaphragm having an aperture size corresponding to the first size and a second diaphragm having an aperture size corresponding to the second size, wherein the diaphragm switching unit is arranged to selectively place the first diaphragm and the second diaphragm in the optical path; and
(c) the diaphragm having an aperture size corresponding to the first size, wherein the diaphragm switching unit is arranged to insert and remove the diaphragm into and from the optical path, and an aperture size on the optical path when the diaphragm is removed from the optical path defines the second size.

* * * * *